United States Patent [19]

Bollinger

[11] Patent Number: 5,427,108
[45] Date of Patent: Jun. 27, 1995

[54] ULTRASONIC DOPPLER PROBE WITH NEEDLE GUIDE

[76] Inventor: Armin Bollinger, Hegetsbergstrasse 28, CH-8610 Uster, Switzerland

[21] Appl. No.: 220,884

[22] Filed: Mar. 31, 1994

[30] Foreign Application Priority Data

Apr. 1, 1993 [CH] Switzerland .................. 01003/93

[51] Int. Cl.$^6$ ............................................. A61B 8/00
[52] U.S. Cl. .................................................. 128/662.05
[58] Field of Search ................. 128/660.01, 660.03, 128/661.07, 661.08, 662.03, 662.04, 662.05

[56] References Cited

U.S. PATENT DOCUMENTS

| | | | |
|---|---|---|---|
| 4,029,084 | 6/1977 | Soldner | 128/662.05 |
| 4,542,747 | 9/1985 | Zurinski et al. | 128/662.05 |
| 4,899,756 | 2/1990 | Sonek | 128/662.05 |
| 5,076,279 | 12/1991 | Arenson et al. | 128/662.05 |
| 5,235,987 | 8/1993 | Wolfe | 128/662.05 |
| 5,261,409 | 11/1993 | Dardel | 128/662.05 |

FOREIGN PATENT DOCUMENTS

| | | |
|---|---|---|
| 1927868 | 6/1975 | Germany . |
| 3202822 | 8/1982 | Germany . |
| 536635 | 6/1973 | Switzerland . |
| 543283 | 12/1973 | Switzerland . |
| 547503 | 3/1974 | Switzerland . |

OTHER PUBLICATIONS

Ultraschall-Doppler in: Anesthesist, Schregel, W., 1985, 34:93-97.

"Doppler Localization of ther Internal Jugular Vein Facilities Central Venous Cannulation", Dwight Leger, et al., Clinical Reports, Anesthesiology 60:481-482, 1984.

Primary Examiner—George Manuel
Attorney, Agent, or Firm—Weingarten, Schurgin, Gagnebin & Hayes

[57] ABSTRACT

An ultrasonic Doppler probe which can be used together directly with a hollow needle for puncturing a blood vessel is disclosed. The hollow needle can be set once the blood vessel sought has been located with the ultrasonic Doppler probe. A needle guide passes concentrically through the probe head. The hollow needle is pushed through the needle guide. It can thus be set with great accuracy. The ultrasonic Doppler probe can be opened in the shape of a wedge in the vicinity of its probe head and the needle guide, permitting it to be removed to the side from the set needle.

18 Claims, 2 Drawing Sheets

5,427,108

ULTRASONIC DOPPLER PROBE WITH NEEDLE GUIDE

FIELD OF THE INVENTION

The invention relates to a probe with a needle guide for the location of blood vessels in the body, and more particularly to an ultrasonic probe with an ultrasonic transmitter and receiver arranged according to the Doppler principle.

BACKGROUND OF THE INVENTION

During work with catheters in the operating room, and in the case of certain other interventions, arteries and veins must be pierced with relatively thick, hollow needles to insert catheters. Arteries and veins are often punctured, which are not highly visible and scarcely palpable through the skin. This creates the problem of locating suitable blood vessels in the body with sufficient accuracy to permit them to be punctured thereafter. The known ultrasonic Doppler technique permits a simple and precise location of the sought blood vessels. It is even thereby possible to determine the direction of flow in the individual blood vessel and thus to distinguish and identify arteries and veins.

Disclosed in patent CH 536,635 (Siemens) is a device in which an ultrasonic Doppler probe is permanently mounted at the upper end of the injection cannula. The probe cannot be withdrawn from the cannula after the puncture is made. The cannula is thus provided with a branch to the side for connection of a syringe or tube. With this arrangement it is possible to insert injection cannulae in blood vessels with great accuracy. This technique has not become widely used in practice.

SUMMARY OF THE INVENTION

An ultrasonic Doppler probe with needle guide for the location of blood vessels in a body and its insertion with a hollow needle, and with an ultrasonic transmitter and receiver arranged according to the Doppler principle.

The purpose of the invention is to create an ultrasonic Doppler probe which can be utilized together with a hollow needle. It should be possible to set the hollow after the blood vessel sought has been located with the ultrasonic probe. It should then be possible to separate and remove the ultrasonic probe from the hollow needle, while the hollow needle remains in position.

A significant advantage of the invention is the option of removing the ultrasonic probe from the needle to the side, after the sought for blood vessel is punctured. As a result there will be no unnecessarily restrictive tubes in the working area of the doctor. An additional advantage is that the ultrasonic Doppler probe also provides a clear indication of the direction of flow in the blood vessel in addition to its location. That permits, for example, an unequivocal distinction to be made between arteries and veins. With the use of a bidirectional Doppler device it is possible to indicate the direction of flow optically at the probe itself. A unidirectional Doppler unit indicates the signals acoustically.

DESCRIPTION OF THE DRAWINGS

The invention will be more fully understood from the following detailed description taken in conjunction with the accompanying drawings in which.

DETAILED DESCRIPTION OF THE INVENTION

A known ultrasonic Doppler probe with ultrasonic transmitter and receiver operates via an electrical connection to a unidirectional or bidirectional Doppler device for signal interpretation. The transmitter in the probe is capable of continuous or pulsed operation. The Doppler unit contains an amplifier and other necessary, known electronic parts. The indicator is either acoustic, through a loudspeaker, or optical, for example, by means of an LED or LCD display.

A simplest embodiment of the invented ultrasonic Doppler probe is executed with a two-part probe head in a unitary holder. Located in one part is the piezo crystal for transmitting and in the other the piezo crystal for receiving. The two parts lie so close together in a plane of separation that the operation of the probe is assured. There is a narrow slot in the probe head, extending from its edge radially inward along the plane of separation into its center. The center of this slot forms a needle guide through the probe head, from top to bottom. Once the blood vessel is located, a hollow needle is passed along this needle guide into the blood vessel. The ultrasonic Doppler probe can be then withdrawn along the slot, to the side of the set needle.

Figure 1:
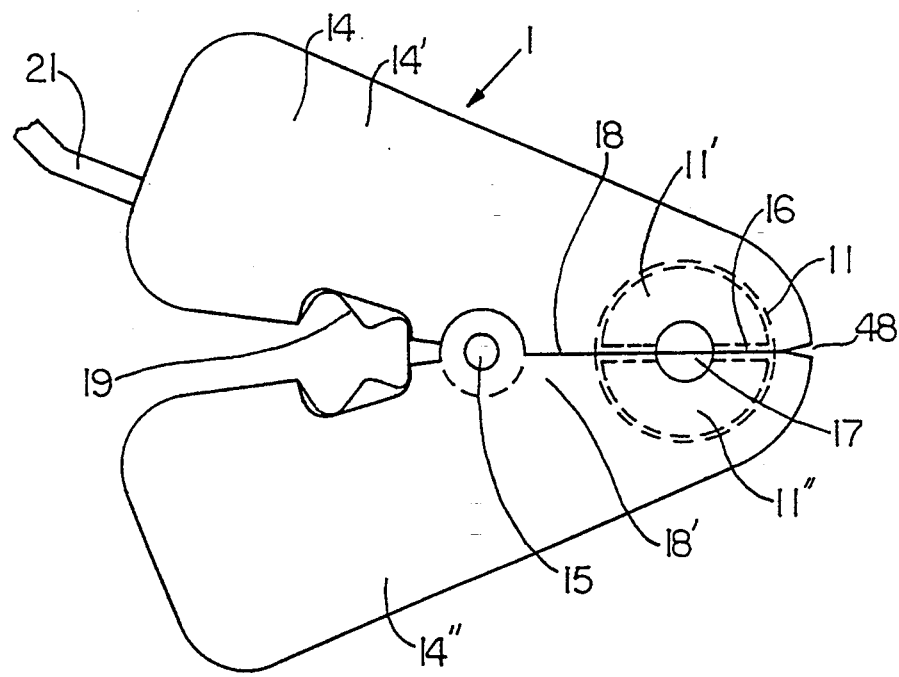
FIG. 1 is a top view of an embodiment of the partable probe head with laterally removable hollow needle.

An optimized embodiment of the ultrasonic Doppler probe 1 is seen in FIG. 1 and includes a holder 14 with a probe head 11. In one embodiment, the holder 14 is a spring-loaded clamp. The holder 14 comprises two clamp halves 14', 14", joined approximately at the center with a hinge 15 on which they pivot, which are held in the rest position by means of a keeper spring 19. The two clamp halves 14, 14" are equipped with clamp sides 18, 18' to one side of the hinge 15. These clamp sides 18, 18' lie tightly together in the rest position. On the opposite side of the hinge 15 are the two clamp halves 14', 14" which form an angle relative to one another The holder 14 can be pressed together at that point, against the force of the keeper spring 19, opening the holder 14 at the end of the clamp sides 18, 18'.

The probe head 11 with the ultrasonic transmitter 11' and receiver 11" is located in the holder 14 near the clamp sides 18, 18' which lie one upon the another. A plane of separation 16 is formed by the clamp sides 18, 18' of the two clamp halves. The plane of separation 16 also therefore passes through the probe head 11, so that this, too, is divided in two. The transmitter 11' is integrated in the clamp side 18 of one clamp half 14'. The receiver 11" is in the clamp side 18' of the other clamp half 14". Sender 11' and receiver 11" lie so close together in the resting and operating positions of the holder 14 that the probe 11 is able to function That is to say, transmitter 11' and receiver 11" in the normal state, due to the pressure of the spring, lie in the correct position to permit location of the blood vessels.

The needle guide 17 is arranged concentrically in the probe head 11 and passes through the probe head 11. This needle guide 17 is likewise split into two halves by the plane of separation 16.

The ultrasonic Doppler probe 1 may be held with one hand and moved upon a body to be examined. The signals from the probe 11 reach the Doppler unit with the known acoustic and/or optical indicator via the cable 21. As soon as the blood vessel sought is located, the hollow needle 5 is pushed through the needle guide 17 into the body until the blood vessel has been punctured. The concentric arrangement of the needle guide 17 in the probe head 11 assures a reliable hit on the located blood vessel. The holder 14 is then pressed together at its open end against the pressure of the keeper spring 19. The holder 14 is thereby spread apart at the plane of separation 16 of the clamp sides 18, 18' and opened in the shape of a wedge, together with the probe head 11 and the needle guide 17. This releases hollow needle 5 and the ultrasonic Doppler probe 1 is able to be withdrawn to the side from the hollow needle 5 now set in the body.

The holder 14 is ergonomically shaped to enable one person to hold, guide and position it with only one hand, leaving the second hand free for the guide and the syringe.

Figure 2:
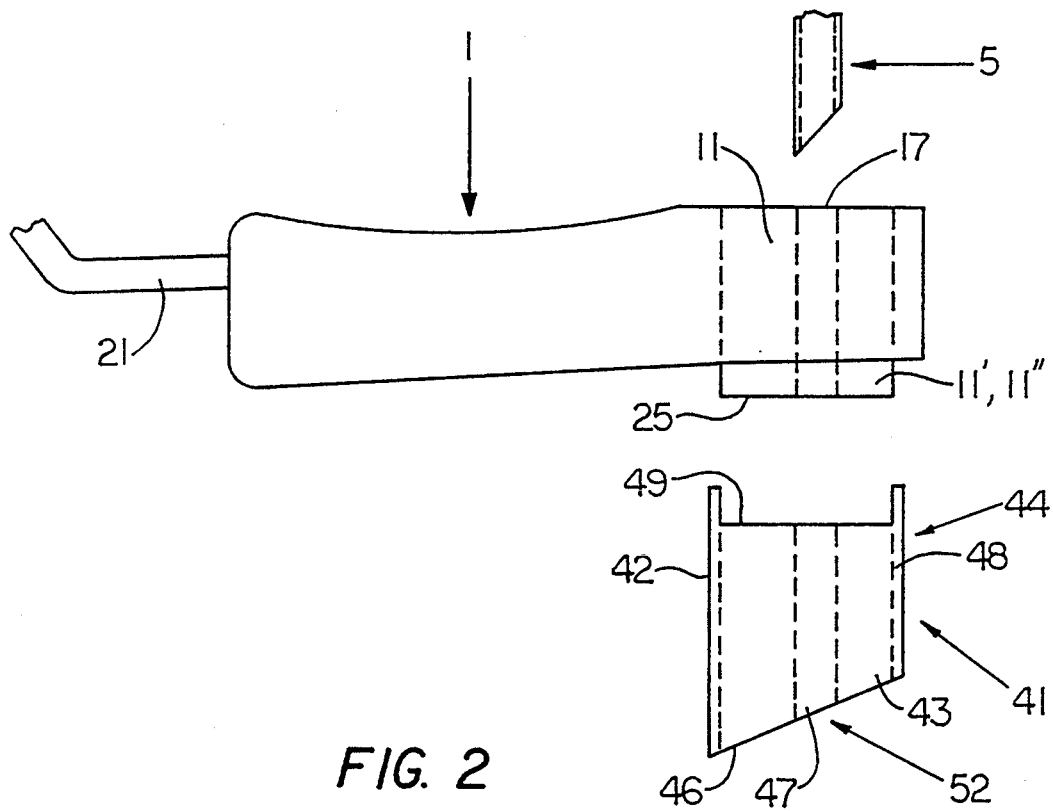
FIG. 2 is a side view of an embodiment of the partable probe head with laterally removeable hollow needle.

In FIG. 2 the ultrasonic Doppler probe is shown from the side. The position of the probe head 11 with transmitter 11', receiver 11" and the needle guide 17 is clearly visible. The transmitter 11' and receiver 11" project downward somewhat below the holder 14 and form there a flat contact surface 25. The contact surface 25 serves to transmit the ultrasonic waves from the probe to a body to be examined. The needle guide 17 forms a right angle with the contact surface 25. This assures a precise setting of the needle in the sought blood vessel.

In one embodiment, the ultrasonic Doppler probe 1 can be equipped supplementarily with a coupler 41 as the element for transmitting sound. The coupler 41 consists of a cylindrical part 42 with a filler 43 made of suitable material with the necessary ultrasonic properties. The coupler 41 partially encloses the probe head. A flat surface 49, when in use, creates the contact with the contact surface 25 of the probe head 11 of the ultrasonic Doppler probe 1. The coupler 41 exhibits a lengthwise borehole 47, from one surface to the other, through which hollow needle 5 can be inserted. Extending radially from the lengthwise bore is a cut constituting a plane of separation 48. This plane of separation 48 corresponds to the separation plane of the probe head and forms its extension in the coupler 41.

The probe head 11 extends downward into a mounted coupler 41 to the point where its contact surface 25 makes contact with the flat surface 49 of the filler. Lateral pressure on the holder 14 opens the partable probe head 11. That also spreads apart shaped part 42. This opens the separation surfaces into a slot. The hollow needle 5 is released. The probe 1 can be removed with the coupler 41 to the side.

The coupler 41 terminates on the side facing the body in a contact surface 46 which slopes relative to the lengthwise axis of the needle guide 17. It is recommended that the angle of the contact surface 46 be approximately 45 degrees. The angle at which the unit is held can be adjusted according to the direction of puncture. That permits the probe to be held in use slightly angled away from the body, thus making it easier to manage. To ensure good ultrasonic conduction, the contact surfaces 46 and 25 as well as the skin must be moistened with sterile water.

Figure 3:
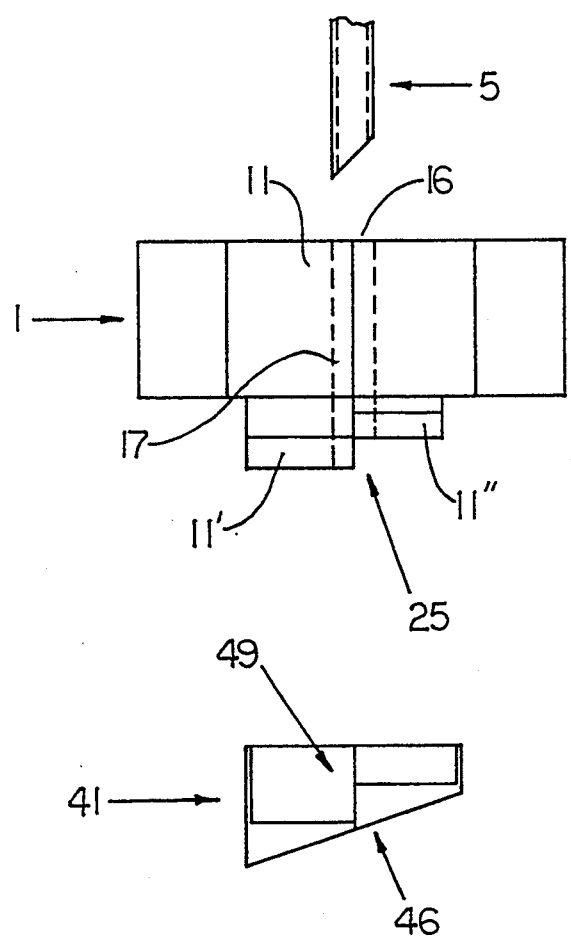
FIG. 3 is a front view of an embodiment of the invention with a partable, stepped probe head.

In FIG. 3, the partable probe is shown seen from the front. The ultrasonic Doppler probe 1 exhibits a partable probe head 11, which is extended downward. In this embodiment the contact surface 25 of the probe head 11, seen from the front, has two steps. The probe head 11 ends in a first step with the transmitter 11' and in a second step which faces it with the receiver 11". The first step extends further downward than the second step. This embodiment must be fitted with a correspondingly shaped coupler. The coupler 41 then exhibits a stepped surface 49. The two-level execution form has the advantage that the coupler 41 will have a lower structural height, permitting the achievement of a slight damping.

Although the invention has been shown and described with respect to an illustrative embodiment thereof, it should be appreciated that the foregoing and various other changes, omissions and additions in the form and detail thereof may be made without departing from the spirit and scope of the invention as delineated in the claims.

What is claimed is:

1. An ultrasonic Doppler probe to locate and puncture blood vessels in a body comprising:
   a holder;
   a probe head coupled to said holder, said probe head having an axial bore therethrough which splits said probe head and forms a needle guide;
   an ultrasonic transmitter; and
   an ultrasonic receiver wherein said needle guide is concentrically arranged in said probe head, and said ultrasonic transmitter and said ultrasonic receiver are mounted in said probe head substantially surrounding the needle guide in said probe head and projecting below a first surface of said probe head by a predetermined distance to provide said probe head having a contact surface through which sound waves are transmitted to the body; and
   a coupler having a first surface coupled to the contact surface of said probe head and a second opposite surface adapted to contact the body wherein the second surface of said coupler is angled with respect to the contact surface of said probe head.

2. The ultrasonic Doppler probe according to claim 1, wherein said probe head is provided having a slot which extends radially from an outside edge of said probe head toward the needle guide and the slot has a width selected to accommodate a width of a needle.

3. The ultrasonic Doppler probe according to claim 1, wherein
   said holder includes a spring-loaded clamp comprising a spring and two clamp halves joined together by a hinge and coupled to said spring, each of said clamp halves having a clamp side wherein said clamp sides contact one another and define a plane of separation; and
   said probe head is arranged in said clamp sides such that said ultrasonic transmitter and said ultrasonic receiver are positioned in respective ones of said two clamp halves and are on opposing sides of the plane of separation.

4. The ultrasonic Doppler probe according to claim 3, wherein in response to compressing said spring said clamp sides are spread apart such that said probe head and said needle guide are spaced apart at the plane of separation.

5. The ultrasonic Doppler probe according to claim 1, wherein the contact surface of said probe head formed by said ultrasonic transmitter and ultrasonic receiver is flat.

6. The ultrasonic Doppler probe according to claim 1, wherein the contact surface of said probe head formed by said ultrasonic transmitter and said ultrasonic receiver has a first portion spaced a first predetermined distance from a first surface of said probe head and a second portion spaced a second predetermined distance from the first surface of said probe head.

7. The ultrasonic Doppler probe according to claim 1, coupler is provided from a material having ultrasonic properties substantially the same as the ultrasonic properties of the body and said coupler is provided having a bore therethrough, wherein a central longitudinal axis of the axial bore in said needle guide is aligned with a central longitudinal axis of said coupler.

8. A probe for locating blood vessels in a body, the probe comprising:
a holder;
a split probe head coupled to said holder, said probe head having an axial bore therethrough which forms a needle guide;
an ultrasonic transmitter;
an ultrasonic receiver wherein said ultrasonic transmitter and said ultrasonic receiver are mounted in said probe head and project below a first surface of said probe head by a predetermined distance to provide said probe head having a contact surface through which sound waves are transmitted; and
a coupler having a first surface coupled to the contact surface of said probe head and a second opposite surface adapted to contact the body wherein the second surface of said coupler is angled with respect to the contact surface of said probe head.

9. The probe of claim 8 wherein said coupler is provided having a bore therethrough, wherein a central longitudinal axis of the axial bore in said needle guide is aligned with a central longitudinal axis of said coupler.

10. The probe of claim 9 wherein the contact surface of said probe head has a first portion spaced a first predetermined distance from the first surface of said probe head and a second portion spaced a second different predetermined distance from the first surface of said probe head.

11. The probe of claim 8 wherein the contact surface of said probe head formed by said ultrasonic transmitter and ultrasonic receiver is flat.

12. The probe of claim 8 wherein the contact surface of said probe head formed by said ultrasonic transmitter and said ultrasonic receiver has a first portion spaced a first predetermined distance from the first surface of said probe head and a second portion spaced a second different predetermined distance from the first surface of said probe head.

13. The probe of claim 8 wherein the probe head is provided having a generally circular shape and the needle guide is centrally and concentrically disposed in said probe head.

14. The probe of claim 13 wherein said ultrasonic transmitter and said ultrasonic receiver are mounted in said probe head to substantially surround the needle guide in said probe head.

15. The probe of claim 14 wherein:
said holder includes a spring-loaded clamp comprising a spring and two clamp halves joined together by a hinge and coupled to said spring, each of said clamp halves having a clamp side wherein said clamp sides contact one another and define a plane of separation; and
said probe head is arranged in said clamp sides such that said ultrasonic transmitter and said ultrasonic receiver are positioned in respective ones of said two clamp halves and on opposing sides of the plane of separation.

16. A probe for locating blood vessels in a body, the probe comprising:
a holder
a probe head coupled to said holder, wherein said probe head is separable along a plane of separation and wherein said probe head is provided having an axial bore therethrough wherein the axial bore is aligned along the plane of separation and forms a needle guide in said probe head;
an ultrasonic transmitter coupled to said probe head; and
an ultrasonic receiver coupled to said probe head wherein said ultrasonic transmitter and said ultrasonic receiver provide said probe head having a contact surface through which sound waves are transmitted; and
a coupler having a first surface having a shape adapted to couple to the contact surface of said probe head and a second surface adapted to contact the body wherein the second surface of said coupler is angled with respect to the contact surface of said probe head, said coupler for transmitting sound between the contact surface of said probe head formed by said ultrasonic transmitter and ultrasonic receiver and the second surface of said coupler and wherein said coupler is provided having a bore therethrough, wherein a central longitudinal axis of the axial bore in said needle guide is aligned with a central longitudinal axis of said coupler.

17. The probe of claim 16 wherein the contact surface of said probe head formed by said ultrasonic transmitter and said ultrasonic receiver has a first portion spaced a first predetermined distance from the first surface of said probe head and a second portion spaced a second different predetermined distance from the first surface of said probe head.

18. The probe of claim 17 wherein:
said probe head is provided having a generally circular shape and the needle guide is centrally and concentrically disposed in said probe head;
said ultrasonic transmitter and said ultrasonic receiver are disposed in said probe head on opposing sides of the plane of separation and are mounted in said probe head to substantially surround the needle guide in said probe head.

* * * * *